United States Patent [19]

Burchiel et al.

[11] 4,311,688

[45] Jan. 19, 1982

[54] COMPOSITION AND METHOD FOR CANCER DETECTION IN HUMANS

[75] Inventors: Scott W. Burchiel, Albuquerque, N. Mex.; David R. Crockford, Nashua, N.H.; Buck A. Rhodes, Albuquerque, N. Mex.

[73] Assignees: Serono Laboratories Inc., Braintree, Mass.; University Patents Inc., Norwalk, Conn.

[21] Appl. No.: 89,153

[22] Filed: Oct. 29, 1979

[51] Int. Cl.$^3$ .................. A61K 49/00; A61K 43/00; B65D 71/00; G01T 1/00
[52] U.S. Cl. ...................... 424/1; 128/659; 260/112 B; 422/61; 424/1.5; 424/9
[58] Field of Search ................ 424/1, 1.5, 9; 260/112 B; 128/659; 422/61

[56] References Cited

U.S. PATENT DOCUMENTS 4,116,776  9/1978  Dalbow et al. .............. 424/12

Primary Examiner—Christine M. Nucker
Attorney, Agent, or Firm—Paul J. Cook

[57] ABSTRACT

Antibody to anti human chorionic gonadotropin and/or antibody to anti human chorionic gonadotropin-beta subunit labeled with technetium-99m, iodine-123, iodine-125 or iodine-131 are/is administered to a human after the human has been administered anti-hCG and/or anti-hCG beta. The biodistribution of the labeled composition accumulates at cancer sites, e.g. tumors that produce human chorionic gonadotropin (hCG), human chorionic gonadotripin-like material, and a compound similar to and/or identical to the beta-chain of chorionic gonadotropin, or mixtures thereof which would bind specifically to anti-hCG and/or anti-hCG-beta.

14 Claims, No Drawings

COMPOSITION AND METHOD FOR CANCER DETECTION IN HUMANS

BACKGROUND OF THE INVENTION

This invention relates to compositions and methods capable of detecting cancer cells or malignant tumors in humans. More particularly, this invention relates to compositions radiolabeled with technetium-99m, Iodine-125, Iodine-131 or Iodine-123 which, when administered to a human will accumulate at cells producing hCG, hCG-like material, and a compound similar to and/or identical to the beta-chain of chorionic gonadotropin, or mixtures thereof.

The use of compositions which emit radiation at levels which can be detected after administration to the human body are well known. These compositions are utilized to visualize and/or monitor functioning of various parts of the body or are utilized diagnostically to determine the presence or absence of particular antigens, antibodies, hormones or the like. In one particular aspect of the prior art, radiolabeled antibodies are utilized to detect tumors having associated therewith carcinoembryonic antigen. As disclosed in U.S. Pat. Nos. 3,663,684, 3,867,363 and 3,927,193, $I^{131}$ or $I^{125}$ labeled antibodies to carcinoembryonic antigen are utilized to detect tumors which produce or are associated with carcinoembryonic antigen. It is also well known that protein molecules can be tagged with technetium-99m in order to form diagnostic agents. It has also been proposed to tag the antibody of the beta chain of human chorionic gonadotropin with peroxidase (McManus et al, Cancer Research, 36, pp. 2367–3481, September, 1976) in order to localize the antigen in malignant tumors. Furthermore, it has been proposed to label the IgG antibody to hCG with radioactive iodine in order to localize the antigen in human choriocarcinomas transplanted in hamster check pouches; Quinones et al (1971), *Journal of Nuclear Medicine*, Vol. 12, No. 2, pp. 69–75.

Recently, it has been found that neoplastic tissues produce and express on their surface chorionic gonadotropin, chorionic gonadotropin-like material, and a compound similar to and/or identical to the beta-chain of chorionic gonadotropin (hCG-beta subunit) or mixtures thereof, specifically to the degree where it is considered a more general marker than either carcinoembryonic antigen (CEA) or alphafetoprotein (AFP), Acevedo et al, "Detection and Prevention of Cancer", Part 2, Vol. I, H. E. Nieburgs (ED) Marcel Dekker, Inc. New York, 1978, pp. 937–979. The positive identification of chorionic gonadotropin in a heterogenous group of cancer cells and its non-detection in non-cancer cells in vitro has suggested that:

(a) this is a unique trophoblastic-like sialoglycoprotein which is synthesized de-novo by the malignant cells;
(b) since CG and/or CG-like glycoprotein has been observed only in the trophoblast and human spermatozoa, its production by the cancer cells can only be explained by an expression of the information which opens the mechanism(s) for its biosynthesis, either by derepression of by an activation of the genetic control;
(c) the compound is a common antigen (common denominator) of every cell with oncogenic properties.

While peroxidase-labeled or fluorescein-labeled anti-hCG-beta or anti-hCG are effective for identifying and localizing malignant cells, these labeled compositions are undesirable for in-vivo use because they do not allow for visualization by any available scintigraphy detection system and are otherwise undesirable for widespread use because they are simply an in-vitro immunohistochemical technique requiring light or electron microscopy or biopsy samples for positive identification. In addition, the use of radiolabeled antibody in scintigraphy wherein the labeled antibody binds directly to the cancer cell having its corresponding antigen can cause faint and imperfect imaging of the cancer cell or cells since the antibody usually has a limited number of binding sites. Thus, the cell may only be able to accomodate one radiolabeled antibody molecule on a single antigen site. Thus, the density of the radiolabeled molecule on the cell surface may not be sufficient to permit distinction of the cancer cell from surrounding tissues.

Accordingly, it would be highly desirable to provide a class or labeled antibodies which can be utilized in-vivo and which overcomes the disadvantages of the prior art compositions.

SUMMARY OF THE INVENTION

In accordance with this invention, radiolabeled compositions are provided which comprise antibodies to anti-hCG-beta or antibodies to anti-hCG which antibodies are labeled with radioactive iodine or Technetium-99m. When using the compositions of this invention to diagnose the presence of cancer cells in a patient, the patient first is administered parenterally anti-hCG or anti-hCG-beta. After a period of time sufficient for the anti-hCG or anti-hCG-beta to accumulate on the sites of the cancer cells which comprise hCG, hCG-beta or hCG like material, the compositions of this invention are administered parenterally. The biodistribution of the labeled compositions is monitored by scintigraphy in order to locate cancer cells or malignant tumors. The present invention provides substantial advantages over the prior art since the compositions provide for higher sensitivity in detecting cancer cells or malignant tumors of the prior art, the technique can be performed in vivo, and the compositions are more effective than compositions utilizing a single antibody approach. The kit contains two components: (1) anti-hCG, anti-hCG-beta, and/or fragments and/or derivatives thereof; and (2) antibody against anti-hCG or anti-hCG-beta or fragments or derivatives thereof. The kit will contain a suitable reducing agent capable of reducing $Tc^{99m}$ from Tc (VII) to Tc (IV), which is added by the user prior to administration to humans. The kit may also contain a chromatographic column containing a material capable of binding Technetium as the pertechnetate or as a complex of Technetium. Alternatively, the kit may contain reagents necessary for the radiolabeling of antibody with either $I^{131}$, $I^{125}$, or $I^{123}$.

DESCRIPTION OF SPECIFIC EMBODIMENTS

Human chorionic gonadotropin (hCG) is a molecule believed to have a molecular weight ranging from about 35,000 and 38,000. HCG is found in the urine and sera of pregnant women, in patients with trophoblastic tumors and in the normal placentas and is produced by certain cell cultures. HCG consists of two noncovalently bonded alpha and beta chains having approximate molecular weights of 14,700 and 23,000 respectively. The alpha and beta chains can be easily dissociated; however, it has been shown that each chain is biologically inactive as a separate entity. The amino acid sequence of the alpha chain has been shown to have close similarity to the alpha chain of luteinizing follicle stimulating hormone and thyroid stimulating hormone. The beta chain has similarity only to the beta chains of luteinizing hormone and less homology to those of follicle stimulating hormone and thyroid stimulating hormone. The beta chain is immunologically active in both the intact hormone and as a separate entity. Approximately 30 percent of the molecule is carbohydrate which is constituted by six different monosaccharides: sialic acid, L-fructose, D-galactose, D-mannose, N-acetylglucosamine and N-acetylgalactosamine.

The source of $I^{125}$, $I^{131}$ and/or $I^{123}$ is commercially obtained by nuclear reactor or cyclotron and in any form suitable for radiolabeling. The iodine molecules are retained on the antibody such as by means of a covalent bond adjacent to the aromatic hydroxyl group tyrosyl or histidyl acid residues, or by recoil labeling from $Xe^{123}$ decay. Therefore, these compositions are relatively stable. However, it is preferred to utilize an antibody labeled with technetium-99m rather than radioactive iodine since technetium 99m affords improved images by scintigraphy. In contrast to the iodine-labeled antibody, technetium-99m is retained by the antibody by a chelation mechanism. Thus, the reagent is formed under reducing conditions in order to minimize or prevent the reversible reaction by which the technetium-99m becomes free of the antibody.

The source of the technetium-99m preferably is water soluble such as the alkali or alkaline earth metal pertechnetate. The technetium can be obtained as sodium pertechnetate Tc-99m from a conventional 99Mo/99mTc generator. Any source of pharmaceutically acceptable technetium-99m may be utilized in the present invention.

Anti-hCG or anti-hCG-beta serum is obtained by any conventional method such as by immunizing animals such as rabbits, sheep, goats or other suitable species with intact hCG or hCG-beta subunit in order to induce production of the hCG antibody or hCG-beta antibody. Serum then is harvested from the immunized animals and the specific anti-hCG or anti-hCG-beta immunoglobulins then can be obtained in sufficiently pure form such as by affinity chromatography, immunoprecipitation, non-immune precipitation or the like. In affinity chromatography, for example, an hCG-rich fraction first is isolated such as from pregnant female serum or urine by conventional nonimmune precipitation or immunoprecipitation techniques followed by chromatography on DEAE-cellulose followed by gel filtration on Sephadex G-100 or by another suitable purification technique. The hCG-rich fraction thus obtained is passed onto a column of a cyanogen halide activated or periodate activated gel such as Sephadex, Sepharose or cellulose or another insoluble polysaccharide with carboxyl, polyhydroxyl or N-hydroxylsuccinimide ester functionality in order to chemically attach the hCG by a weak covalent bond to the gel. The serum obtained from the animal then is passed through the column and the anti-hCG or anti-hCG-beta becomes specifically attached to the hCG, its corresponding antigen, in the column while the remainder of the other immunoglobulins and non-specific antigens pass through the column. The anti-hCG or anti-hCG-beta then is recovered from the column by passing an appropriate buffer, e.g. acetate or phosphate solution through the column in order to break the weak covalent bond between the anti-hCG or anti-hCG-beta and the hCG-gel matrix. The anti-hCG-beta or anti-hCG can be obtained in any conventional manner such as by elution with solution or buffer of appropriate ionic strength and pH.

After the anti-hCG-beta is isolated, an antibody to anti-hCG or an antibody to anti-hCG-beta hereinafter referred to as a second antibody is produced in an animal species other than the species used to produce the anti-hCG or anti-hCG-beta hereinafter referred to as the first antibody by either of the two procedures described below:

(1) An animal of a species different from the species in which the first antibody was produced is immunized with a non-immune IgG fraction (normal IgG) of immunoglobulin from an animal species used in obtaining the first antibody in order to produce a desired second antibody which binds to first antibody or:

(2) Immune IgG fraction (anti-hCG-IgG) from the animal used to produce the first antibody is administered to an animal of a different species to produce a desired second antibody which binds to its first antibody.

The process for obtaining the composition of this invention is illustrated by the following schematic route:

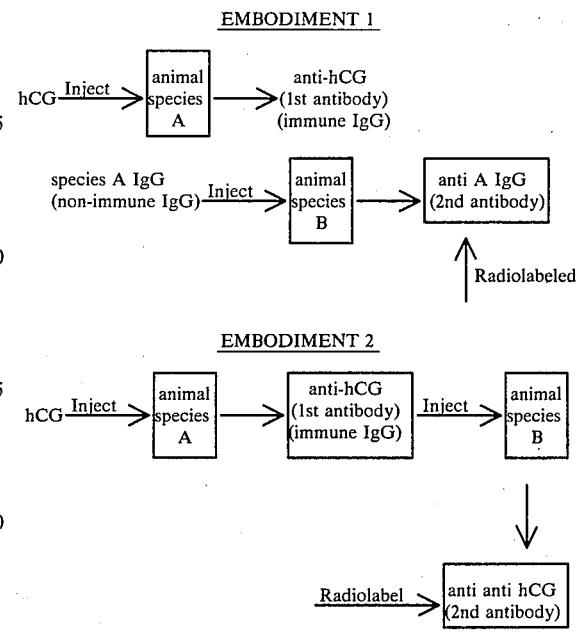

It is to be understood that the above schematic routes are merely exemplary and that hCG-beta or a mixture of hCG and hCG-beta can be utilized initially rather than hCG. Also, it is to be understood that animal species A is not a human. It is preferred to utilize Embodiment 1 because the second antibody produced therefrom will bind specifically to any immune IgG which immunogen (antigen) came from the animal species used to produce the immune IgG. Serum containing second antibody then is harvested and the second antibody is obtained in purified form as for example by the procedures set forth above for the anti-hCG or anti-hCG-beta.

It is to be understood that the method of forming the antibodies is not critical to the present invention so long as they are in sufficiently pure form as to render the composition immunoreactive for their respective antigens. An alternative method for forming the antibodies useful in the present invention comprises the method for making antibody producing hybridomas disclosed by Kohler and Milstein (1975) Nature, Vol. 256, pp. 495–497.

It is to be understood also that while the present invention is described specifically with respect to the use of two antibodies in series, the present invention is not limited to a series of only two antibodies, the second of which is radiolabeled. In order to provide higher concentrations of the radioisotope located on the tumerous cell, a series of three or more antibodies may be utilized, the last of which is radiolabeled. By operating in this manner, the number of available sites associated with the tumerous cell for attachment of the radiolabeled antibody is increased greatly. The series of suitable antibodies is made as described above, with the only restrictions being that the antibodies adjacent in the series are produced from animal species different from the next adjacent antibodies in the series and that the first antibody produced in the series is anti-hCG or anti-hCG-beta. These procedures are shown schematically as Embodiments 3 and 4.

EMBODIMENT 3

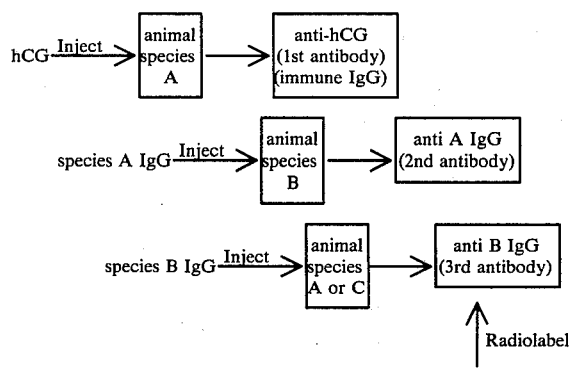

EMBODIMENT 4

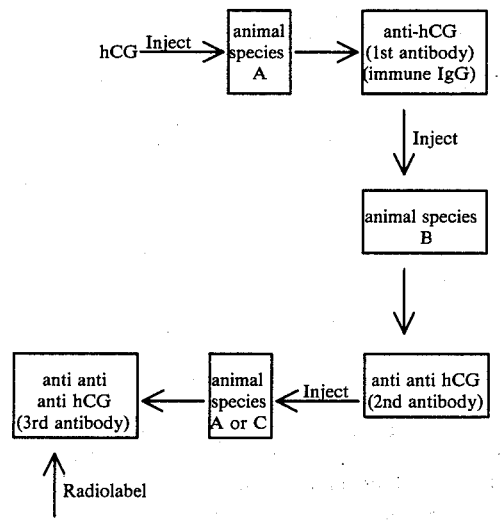

The antibodies are administered parenterally to the patient in the same sequence as they are produced with the radiolabeled antibody being administered last. That is, the first antibody obtained as described above is administered first. Subsequently, the second antibody is administered to produce a third antibody which is radiolabeled. The last antibody in the series of antibodies will be referred to as the "last antibody". The primary limitation on the number of antibodies that are administered is the possibility that the patient will experience undesirable side reactions to the antibodies. The possibility of undesirable side reactions occurring may be reduced by the use of antibody fragments obtained by conventional techniques.

The technetium-99m labeled antibody to anti-hCG or antibody to anti-hCG-beta is prepared by acidic, basic or neutral (ligand-exchange) radiolabeling techniques. In one particular and preferred aspect of this invention, the technetium-labeled antibody to anti-hCG or antibody to anti-hCG-beta is obtained by a ligand exchange process. In this process, a solution of technetium (IV) is prepared by mixing a solution of technetium such as in the form of a pertechnetate ($TcO_4^-$) and saline with a stannous reducing solution, e.g. stannous fluoride-acetate having a pH between about 3 and 5.5. In this procedure, the stannous ions reduce technetium (VII) to technetium (IV). The reduced technetium-99m first is chelated onto the top of a column of Sephadex G-25 (dextran cross-linked with carboxyl functionality) by passing the aqueous solution of technetium-99m through the column. The solution has a pH between about 5.5 and 7.0. The column then is washed with saline to essentially remove free pertechnetate ($TcO_4^-$) or unusual species of technetium thereby leaving the technetium-99m chelated or absorbed or otherwise bound to the column. A physiologic solution of the antibody to anti-hCG and/or the antibody to anti-hCG-beta then is prepared with appropriate buffer so that the resultant solution has a pH between about 6 and 9, preferably between about 7 to 8. When operating within this pH range, denaturation of the antibody to anti-hCG or the antibody to anti-hCG-beta is eliminated or minimized. The protein is then added in a minimum volume to the top of the column where the technetium-99m/Stannous complex is bound and where it is allowed to stand until the technetium-99m is bound to the protein having stronger bonding sites than the column material. This usually occurs within about 30 minutes. The column then is washed to remove the labeled antibody to anti-hCG or antibody to anti-hCG-beta. Washing can be effected with a known volumn of human serum albumin diluted with 50/50 ACD or the like followed by a known volume of saline. In this manner, the volume of washing saline solution containing the labeled protein can be determined and the labeled protein can be collected. Impurities in the antibody to anti-hCG or antibody to anti-hCG-beta will remain on the column or will be eluted at a rate different from that of the labeled, immunologically intact, antibody to anti-hCG or antibody to anti-hCG-beta.

A second preferred method for forming technetium-99m labeled antibody to anti-hCG or antibody to anti-hCG-beta comprises direct labeling of the protein. In this method, a buffered solution is admixed with an acidic solution of $SnCl_2$ which is a reducing agent for pertechnetate. The buffered solution can comprise sodium and/or potassium phthalate, tartrate, gentisate, acetate, borate or mixtures thereof having a pH of between 4.5 and 8.0, preferably about 5.5. Tartrate is utilized to maintain the appropriate concentration of stannous ion in solution to effect the desired solution pH. The $SnCl_2$ preferably is added to the buffer as a solution with concentrated HCl. Thereafter, the solution is neutralized such as with sodium hydroxide to attain a pH of between about 4.5 and 8.0, preferably about 5.5. The antibody to anti-hCG and/or antibody to anti-hCG-beta then is added to the neutralized solution in an amount to attain a concentration of protein up to just less than that which would begin to precipitate the protein in the buffer being used. In order to attain the desired degree of protein labeling, the resultant stannous ion, buffer, protein solution is allowed to incubate. For example, at room temperature, the incubation time should be at least about 15 hours, preferably at least about 20 hours under a nitrogen or an inert gas atmosphere. If desired, this solution can be heated moderately to reduce the incubation time. The solution then can be either freeze-dried and subsequently reconstituted for admixture with pertechnetate or can be admixed directly with pertechnetate solution to obtain the labeled protein. If desired, the resultant radiolabeled protein may be further purified to separate the labeled protein from free technetium such as by chromatography in a Sephadex column. However, this last step is optional.

The present invention also provides a kit with which a user can prepare the composition of this invention and administer it to a patient relatively quickly after preparation. The kit includes each antibody either in lyophilized form, frozen or liquid of suitable ionic strength and pH, and either containing or not containing a reducing agent. If without the reducing agent, the final antibody can be admixed with a reducing solution or solid provided within the kit and in a separate container. Representative, suitable reducing agents are $SnCl_2$ or $SnF_2$ to be dissolved or already dissolved in an appropriate solution, such as sodium acetate/acetic acid, acidified deionized or distilled water, or the like, such that a reducing pH of about 3 to 8.0 is obtained when combined with technetium-99m as as sodium pertechnetate. Therefore, technetium-99m as pertechnetate is either reduced in the presence of reducing agent prior to addition of the final antibody or is reduced when added to the final antibody containing reducing agent. The solution of labeled final antibody is then suitable for administration to a patient.

In forming the technetium-labeled products of this invention, a solution of the technetium-99m as the pertechnetate is poured onto the column in order to bind the technetium thereon. A physiologically acceptable aqueous solution of the final antibody then is poured onto the column in order to bind the labeled technetium to the final antibody. The labeled protein then is eluted from the column with saline or an otherwise appropriate buffer and is collected from the bottom of the column in a form suitable for intravenous administration to a patient. In an alternative embodiment, the eluted labeled protein is passed through a bed of anion exchange resin in order to remove free pertechnetate from the labeled protein thereby to form a pure labeled final antibody substantially free of radiochemical contamination. If desired, these anion exchange resins need not be a part of the columns utilized for labeling but can comprise a separate bed through which the labeled protein is passed.

In an alternative embodiment of this invention, the kit can include a container for a column of material which entraps or otherwise binds technetium-99m such as Sephadex, Sepharose or cellulose. The column of this material also can contain the reducing agent for technetium or the reducing agent can be added thereto when it is desired to reduce the technetium.

The present invention may also provide a kit which contains each antibody either in lyopholized form, frozen, or liquid or suitable ionic strength and pH. The final antibody is radiolabeled with any of $I^{131}$, $I^{125}$, or $I^{123}$ using the chloramine T/sodium metabisulfite method, or other suitable method for covalently linking radioiodine atoms to antibody molecules. The components of this kit will be essentially the same as those for the kit employing $Tc^{99m}$, with the exception of reagents necessary for radiolabeling.

The labeled final antibody is administered by intravenous injection in a pharmaceutically acceptable saline solution, sterile and pyrogen-free. Suitable dosages are usually between about 0.5 and 30 millicuries, preferably between about 10 and 20 millicuries of technetium-99m final antibody for the normal 70 kg. patient. A lesser amount is required when radioiodine is used. The patient then can be scanned by conventional scintigraphy within 1 hour to about 5 days after administration of the labeled protein. Tumors are located in those areas showing a high concentration of labeled final antibody.

It should be understood that the procedure of this invention also can be based upon antigens other than hCG or hCG-beta which are tumor specific such as carcinoembryonic antigen, alpha fetoprotein antigen, or other tumor specific markers wherein one or a series of antibodies are produced as described above and the last produced antibody is radiolabeled.

The following examples illustrate the present invention and are not intended to limit the same.

EXAMPLE I

This example illustrates the preparation of antibody to anti-hCG which can be radiolabeled for use in the present invention. The anti-hCG (sheep) is obtained from Serono Laboratories, Inc. The last antibody was prepared by injecting rabbits with normal sheep IgG in saline. After allowing for an incubation period, the rabbits were bled and the IgG fraction was recovered by gel chromatography, and purified by affinity chromatography. The IgG fraction was shown to have significant activity as the antibody for sheep IgG by the Ouchterlony immunodiffusion method.

EXAMPLE II

This example illustrates a ligand exchange process for obtaining the technetium-99m labeled antibody to anti-hCG of the present invention. The antibody to anti-hCG was obtained by the procedure of Example I. Technetium-99m is obtained from New England Nuclear Corporation. To 0.1 to 5.0 ml of an aqueous solution of Sodium Pertechnetate Tc-99m (pH 5 to 7) is added 0.1 ml of an aqueous acetate solution containing stannous fluoride, pH 3 to 5.5. The stannous ions reduce the pertechnetate ions to technetium IV. The solution then is poured onto a sterile 5 cc column of Sephadex G-25 and then the reduced technetium is bound to the very top of the column. The column then is washed with saline (NaCl) solution to remove any free pertechnetate and other unbound species of technetium. A solution of proper ionic strength and pH containing the IgG fraction containing the antibody to anti-hCG is added to the top of the column. After about 30 minutes, substantially complete ligand exchange occurs to bind the technetium to the antibody. The column then is washed with 1 cc of human serum albumin diluted 50/50 with ACD (Acidified-Citrate-Dextrose). After the albumin solution has soaked completely into the column, 5 cc of saline is added to the column, and the sixth cc of eluate is collected which contains the technetium-99m antibody to anti-hCG.

EXAMPLE III

This example illustrates a direct method of labeling to form the antibody to anti-hCG of this invention. The second antibody is obtained by the procedure of Example I. Technetium-99m is obtained from New England Nuclear Corporation.

To 0.4 ml of a 50 mM of sodium-potassium tartrate buffer (pH 5.50) (10.51 g/l, Ph adjusted to 5.50 with 50 mM tartaric acid) is added 1.6 ml of a 50 mM potassium biphthalate buffer (pH 5.50) (10.21 g/l, pH adjusted to 5.50 with 10 N NaOH). To the resultant buffer solution is added 0.02 ml of 0.5 M $SnCl_2$-HCl (94.8 g/l conc. HCl). The resultant solution is titrated back to a pH of 5.65±0.05 by adding thereto 0.02 ml of 10 N NaOH and the resultant solution is adjusted to a pH of 5.65±0.05 with 1 N NaOH. To this solution is added 0.3 ml of a saline solution of the antibody to anti-hCG (10 mg protein/ml saline). The reaction vessel is allowed to stand approximately 21 hours at room temperature under a nitrogen atmosphere. This solution may be freeze-dried to make a $Tc^{99m}$-labeling kit. Thereafter, 0.2 ml of $NaTcO_4$ with an activity of 0.02-20 mci is added to protein-containing composition and allowed to stand about 1 hour to effect substantially complete labeling of the protein prior to use, the resultant product is passed through a Sephadex column to remove free technetium from the labeled product.

EXAMPLE IV

This example illustrates that the technetium-99m labeled antibody obtained by the procedure of Example III is useful in selectively binding to cancer cells that have been contacted with anti-hCG.

Cancer cells of the type set forth in Table I were reacted in vitro in two steps. (1) Approximately $10^6$ cells were exposed to either normal sheep IgG or sheep anti-hCG (IgG) obtained by the procedure of Example III for thirty minutes at room temperature; cells were then washed three times with a balanced salt solution containing 1% human serum albumin (BSS+1% HSA) using centrifugation to remove unbound antibody. The cells were then incubated for thirty minutes at room temperature with rabbit anti-sheep IgG labeled with $Tc^{99m}$ obtained by the procedure of Example III; cells were then washed with BSS+1% HSA solution and cell pellets were subsequently counted for radioactivity using a gamma counter.

In Table I, specific binding ratio is defined as the ratio of hCG specific binding obtained from cancer cells divided by the hCG specific binding obtained from normal cells. Cell suspensions used for binding studies were lysed with the addition of a 1 N NaOH solution. Cell lysates were then quantitated for protein content using 280 nm absorbance via a dual beam spectrophotometer. The concentration of protein (mg/ml) was determined for each cell suspension, in order to correlate the amount of radioactivity (CMP) as a function of cell number. Using this system, it was found that normal human peripheral blood leukocytes had 194 CPM/mg protein of hCG specific binding, whereas normal human bone marrow had hCG specific binding of 201 CPM/mg protein. The average value of these two normal tissues (i.e., 198 CPM/mg protein) was used as the amount of binding to normal tissue. All tumor cell data is expressed as the ratio of hCG specific binding obtained from normal cells (i.e., BeWo had 3.52 times as much activity as did the normal control samples). Those values that are greater than 1.0 indicate preferential uptake of the anti-hCG antibody on tumor cells. Specific binding ratios greater than about 1.25 are sufficient to localize tumors using gamma scintigraphy.

EXAMPLE V

This example demonstrates that a radioiodinated antibody obtained by the following procedure is useful in selectively binding to cancer cells hat have been contacted with anti-hCG.

Antibody to anti-hCG, as prepared in Example I, was iodinated with $I^{125}$ as follows: To 100 μl of 0.1 m sodium phosphate buffer at a pH of 7.5 was added 25 μl of rabbit anti-sheet IgG in saline (40 mg/ml, 1 mg). To the resultant solution was added 5 μl of sodium iodine ($I^{125}$).

Thereafter, 50 μl (1 mg/ml) of chloramine T in 0.01 M phosphate buffer was added in order to initiate iodination. The resultant solution was incubated at room temperature for about four minutes and thereafter was mixed with 50 ml of 2.4 mg/ml sodium metabisulfite in 0.01 M sodium phosphate buffer in order to stop the reaction. This solution then was incubated at room temperature for about two minutes. Thereafter, 0.3 ml of 1% bovine serum albumin (BSA) in 0.1 sodium phosphate buffer was added in order to serve as a carrier protein. The composition then was passed through a 1X8-200 Dowex column prewashed with 1% BSA to separate free iodine from the composition.

The iodinated sample recovered from the column was used as described in Example IV for testing of the binding of this reagent in association with the anti-hCG reagent to human cancer cells in vitro. The results of this experiment are shown in Table II, whereby it is demonstrated that cancer cells are radiolabeled with these reagents in preference to normal cells.

TABLE I

| Cell Name | Cell Type | $Tc^{99m}$-anti-anti-hCG Specific Binding Ratio |
| --- | --- | --- |
| BeWo | choriocarcinoma | 3.52 |
| JEG | choriocarcinoma | 8.30 |
| HeLa | cervical carcinoma | 2.21 |
| HT-1080 | fibrosarcoma | 4.81 |
| RPMI-8226 | multiple myeloma | 5.04 |
| WI-38 | SV-40 transformed lung | 8.74 |
| HL-60 | acute myeloid leukemia | 4.06 |
| RAJI | Burkitt lymphoma | 2.94 |

As shown in Table I, specific binding ratios greater than 1.25 were obtained for all of the human cell lines tested. Thus, the process of this invention is shown to be useful in selectively identifying cancer calls through the preferential binding of anti-hCG antibodies.

TABLE II

| Cell Name | Cell Type | $I^{125}$-anti-anti-hCG Specific Binding Ratio |
| --- | --- | --- |
| HeLa | cervical carcinoma | 1.85 |
| HT-1080 | fibrosarcoma | 2.07 |
| RPMI-8226 | multiple myeloma | 2.13 |
| WI-38 | SV-40 transformed lung | 1.96 |
| HL-60 | acute myeloid leukemia | 1.71 |

TABLE II-continued

| Cell Name | Cell Type | $I^{125}$-anti-anti-hCG Specific Binding Ratio |
|---|---|---|
| RAJI | Burkitt lymphoma | 1.22 |

As shown in Table II, a radioiodinated antibody to anti-hCG also can be useful in preferentially binding to cancer cells, and thus are capable of identifying the presence of these cells in the body. However, for this latter purpose $I^{131}$ and $I^{123}$ would be preferred radioisotopes, because they are detectable in gamma scintigraphic scans.

We claim:

1. A composition of matter comprising a radiolabeled antibody, said radiolabeled antibody either:
    (a) being directly reactive with an antigen from the group consisting of anti-human chorionic gonadotropin, anti-human chorionic gonadotropin beta and mixtures thereof; or
    (b) being reactive with a second antibody which is directly reactive with said antigen, said reactivity with said second antibody either being direct or through a series of at least one third antibody, the last of said series being directly reactive with said second antibody, said radiolabel consisting of technetium-99m.

2. The composition of claim 1 wherein said antigen is anti-human chorionic gonadotropin.

3. The composition of claim 1 wherein said antigen is anti-human chorionic gonadotropin-beta.

4. The composition of any one of claims 1, 2 or 3 wherein said radiolabeled antibody is directly reactive with said antigen.

5. The process of detecting cancer cells and/or a malignant tumor in a human which comprises injecting into the human an antigen selected from the group consisting of anti-human chorionic gonadotropin, anti-human chorionic gonadotropin-beta and mixtures thereof, subsequently injecting into the human the series of antibodies of claim 1 in the sequence said antibodies are produced with the last of said injected antibodies being said labeled antibody, the time between injections being sufficient to allow substantially all of said antigen and said antibodies not bound to said cells and/or tumor to be metabolized and monitoring the biodistribution of the radiolabeled antibody in said human.

6. The process of claim 5 wherein said antigen is anti-human chorionic gonadotropin.

7. The process of claim 5 wherein said antigen is anti-human chorionic gonadotropin-beta.

8. The process of any one of claims 5, 6 or 7 wherein said radiolabeled antibody is directly reactive with said antigen.

9. A diagnostic kit suitable for forming a composition useful in identifying a cancer cell and/or a malignant tumor which comprises a sterile package containing an antibody either:
    (a) being directly reactive with an antigen selected from the group consisting of anti-human chorionic gonadotropin, anti-human chorionic gonadotropin beta and mixtures thereof; or
    (b) being reactive with a second antibody which is directly reactive with said antigen, said reactivity with said second antibody either being direct or through a series of at least one third antibody, a packaged sterilized reducing agent for technetium, and means for mixing the contents of said sterile package with reduced said reducing agent for technetium-99 m in a physiologically acceptable aqueous solution.

10. The kit of claim 9 wherein a physiologically acceptable reducing agent useful in reducing technetium (VII) to the technetium (IV) state is admixed with said protein.

11. The kit of claim 9 wherein said protein in said sterile package is lyophilized.

12. The kit of claim 10 wherein said protein and reducing agent are lyophilized.

13. The kit of claim 9 which includes a column of material for binding technetium in the IV state and of releasing said technetium when contacted with a solution of said antibody.

14. The kit of claim 9 which includes an ionic exchange resin for selectively removing pertechnetate ion from a solution containing pertechnetate ion from a protein labeled with technetium-99m.

* * * * *